(12) United States Patent
Bonaldo et al.

(10) Patent No.: US 6,287,282 B1
(45) Date of Patent: Sep. 11, 2001

(54) SYRINGE SAFETY SLEEVE AND ADAPTOR

(75) Inventors: Jean M. Bonaldo, Upland; James C. Hagin, Claremont, both of CA (US)

(73) Assignee: Creative Plastic Technology, LLC, Upland, CA (US)

( * ) Notice: Subject to any disclaimer, the term of this patent is extended or adjusted under 35 U.S.C. 154(b) by 0 days.

(21) Appl. No.: 09/440,990

(22) Filed: Nov. 16, 1999

(51) Int. Cl.[7] ................................................. A61M 5/32
(52) U.S. Cl. ............................................ 604/198; 128/919
(58) Field of Search .................................... 604/181, 187, 604/188, 192, 198, 197; 128/919

(56) References Cited

U.S. PATENT DOCUMENTS

| | | | |
|---|---|---|---|
| 5,217,437 | * | 6/1993 | Talonn et al. . |
| 5,415,645 | * | 5/1995 | Friend et al. ........................ 604/110 |
| 5,817,064 | * | 10/1998 | DeMarco et al. .................... 604/198 |
| 5,984,899 | * | 11/1999 | D'Alessio et al. ................... 604/198 |
| 6,017,329 | * | 1/2000 | Hake ..................................... 604/198 |

* cited by examiner

*Primary Examiner*—Sharon Kennedy
*Assistant Examiner*—Catherine Serke
(74) *Attorney, Agent, or Firm*—Roth & Goldman

(57) ABSTRACT

A protective sleeve and adaptor hub combination for retrofitting conventional medical syringes so that the syringe needle may be completely enclosed in the protective sleeve following use of the syringe. The protective sleeve is typically made of polypropylene plastic whereas the adaptor hub which fits in the protective sleeve is made of a harder material Such as polycarbonate. The adaptor hub has internal male threads of hardness suitable for penetrating and cutting female thread grooves in the relatively soft material of a nozzle end of a medical syringe during relative rotation of the protective sleeve and adaptor hub combination and the syringe. Once connected, the hub and sleeve cannot be removed from the syringe. The protective sleeve also has internal spiral tracks and the hub has external follower projections engaged in the tracks for guiding movement of the adaptor hub in the protective sleeve. The sleeve and hub also have an engageable mating annual rib and recess which restrains axial movement of the hub and an attached syringe in the sleeve.

18 Claims, 4 Drawing Sheets

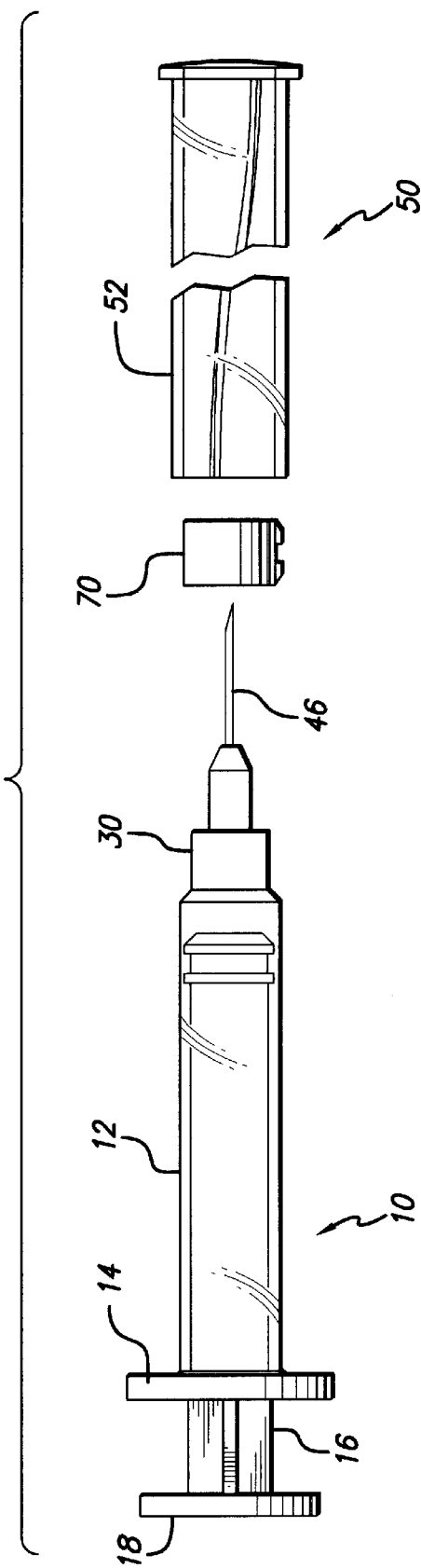

SYRINGE SAFETY SLEEVE AND ADAPTOR

BACKGROUND OF THE INVENTION AND PRIOR ART

The present invention relates to medical syringes for safely drawing blood or other fluid from a patient or for injecting a patient with medication of the type in which a protective sleeve is provided into which a hypodermic needle can be withdrawn and contained after use for safe disposal.

It is well known that protection of medical personnel from contaminated blood or other bodily fluids with which the medical personnel may come into contact during use of medical syringes is highly desirable if not essential in keeping with current medical safety standards.

OBJECTS OF THE INVENTION

It is therefore the primary object of the invention to provide an adaptor and protective sleeve combination for hypodermic syringes in which the adaptor may be easily and permanently affixed to the syringe without special tools by medical personnel or others and wherein the adaptor cooperates with the protective sleeve into which the syringe needle may be withdrawn after use.

It is a further object of the invention to provide a reliable syringe adaptor and protective sleeve combination for converting a conventional non-safety syringe to a safety syringe in which the adaptor and protective sleeve do not contact the syringe flow path and therefore need not be sterile and which is comprised of a small number of parts, each of which are easily formed in mass production.

It is a further object to provide a syringe and protective sleeve combination which meets the foregoing objectives.

SUMMARY OF THE INVENTION

The present invention accordingly provides a protective sleeve and adaptor hub combination for affixation to a medical syringe to enclose a needle affixed to the syringe following use thereof, said combination comprising:

a) an elongate generally cylindrical protective sleeve for telescopically enclosing a syringe, said sleeve having a track on an interior surface for receiving an external follower projection on an adaptor hub as said sleeve is affixed to said adaptor hub; and b) a generally cylindrical adaptor hub sized to internally receive a needle support hub of a medical syringe axially in said adaptor hub, said adaptor hub having at least one internal male screw thread having a sharp leading end for penetrating relatively soft material of a syringe needle support hub during rotation of said adaptor hub relative to said needle support hub as said adaptor is screwed onto a support hub, said adaptor hub further having at least one external follower projection on an exterior surface for engagement with said track in said sleeve for guiding said hub in said sleeve for movement longitudinally of said sleeve; and c) said sleeve and said hub having an engageable mating annular rib and recess for restraining axial movement of said hub and an attached syringe in said sleeve.

The present invention further provides a medical syringe including a housing having a needle support hub, a plunger in said housing and a needle affixed to said needle support hub, a protective outer sleeve for enclosing said needle following use thereof, said protective sleeve telescopically enclosing said syringe housing, and an adaptor hub affixed to said needle support hub and said outer sleeve, said adaptor hub internally receiving said needle support hub axially in said adaptor hub, said adaptor hub having at least one internal male screw thread having a hard sharp leading end penetrating relatively soft material of said needle support hub during rotation of said adaptor hub relative to said needle support hub as said adaptor hub is screwed onto said support hub, said sleeve having a track on an interior surface and said adaptor hub having at least one follower projection on an exterior surface engaged with said track in said sleeve for guiding said hub in said sleeve for movement longitudinally of said sleeve, and said sleeve and said hub having an engageable mating rib and recess for restraining axial movement of said hub and attached syringe in said sleeve.

BRIEF DESCRIPTION OF THE DRAWINGS

In the accompanying drawings:

FIG. 1 is a plan view of a conventional hypodermic syringe, an adaptor hub and a protective sheath into which the syringe needle can be withdrawn.

FIG. 2 is a longitudinal cross sectional view of the protective sheath.

DESCRIPTION OF THE PREFERRED EMBODIMENT

Figure 4:
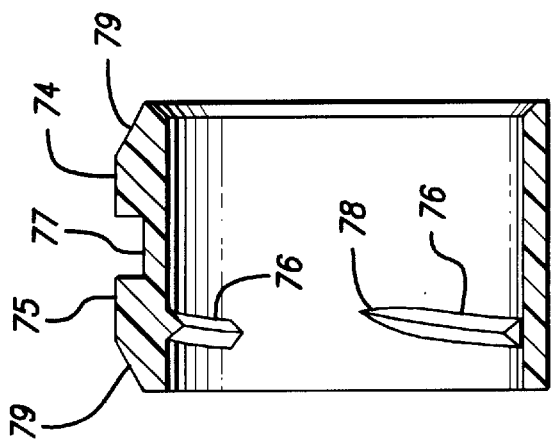
FIG. 4 is a plan view, partly in cross section, of the adaptor hub.

FIG. 1 shows a typical conventional unprotected syringe 10 having an integrally formed cylindrical housing 12, gripping collar 14 and nozzle end 30 preferably integrally formed of polypropylene plastic material. A movable plunger 16 having a gripping collar 18, elongated stem 20 and elastomeric seal at the inner end of the plunger 16 is axially movable in the syringe housing 12. The nozzle end 30 includes cylindrical outer section or skirt 32 and inner section or nozzle 36 which are radially spaced apart so that a needle assembly 40 comprised of a plastic needle support 42 having a collar 44 thereon which supports a hypodermic needle 46 can be threaded into the annular space between the outer section or skirt 32 and inner section or nozzle 36. For this purpose female Luer threads 34 are provided on the inside surface of the outer section or skirt 32 to mate with the edge of the collar 44. The entire needle assembly 40 including the needle support end 42, collar 44 and hypodermic needle 46 is thus easily affixed to the nozzle end 30 of the syringe by screwing the needle support 42 into the Luer threads 34 in a clockwise direction as is known in the art.

Typically, a hypodermic syringe is shipped with a needle attached and with a removable protective plastic sheath (not shown) covering the projecting end of the needle 46 prior to use.

Figure 8:
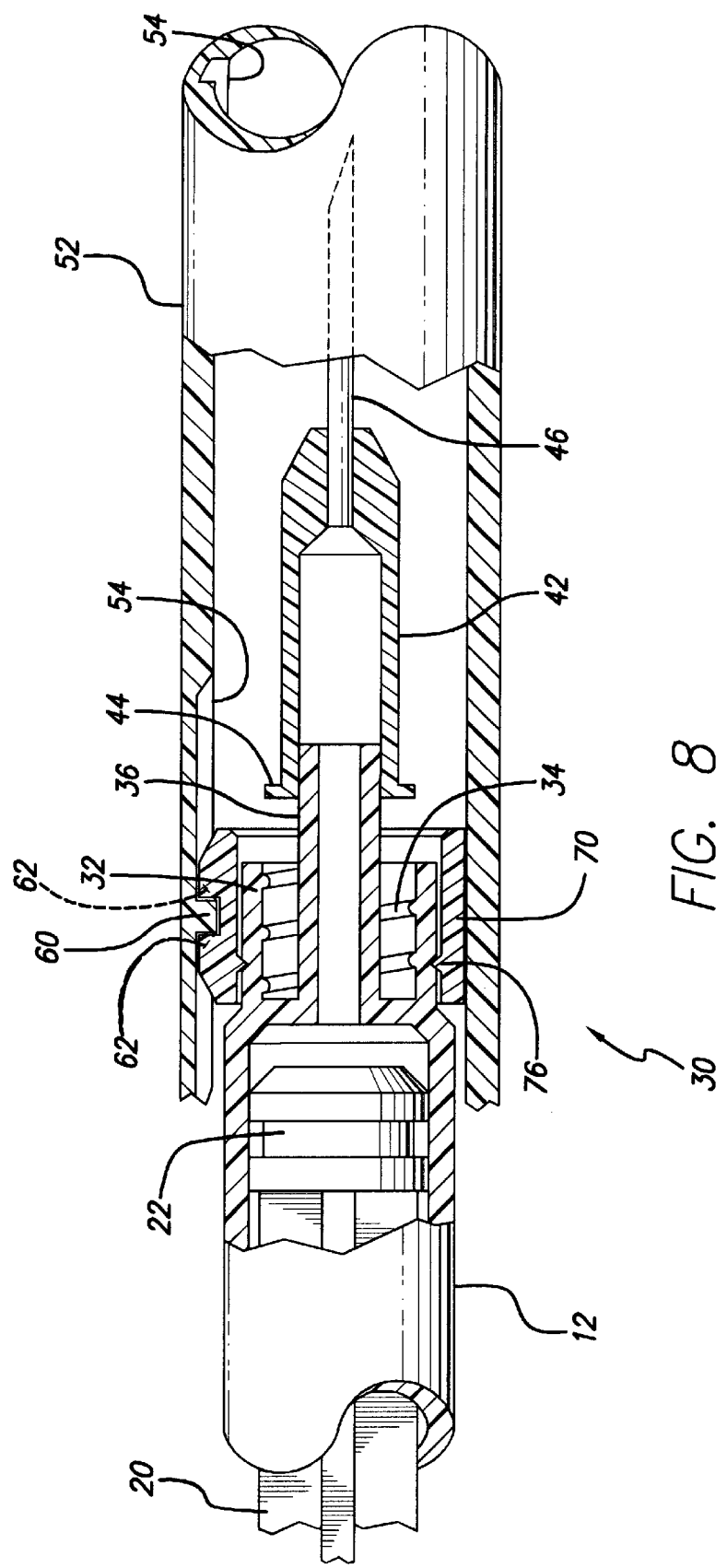
FIG. 8 is a cross sectional view, to a greatly enlarged scale, of the hub held in its final position by an annular rib inside the sheath.

Pursuant to the invention a protective sleeve 50, typically made of polypropylene plastic is provided, the sleeve 50 having a cylindrical wall 52 having at least one end preferably three long pitch spiral internal tracks 54 extending lengthwise of the sleeve from an open end (seen at the left in FIGS. 1 and 2) to a transversely extending sleeve collar 56 having an open aperture 58 at the other end. Also integrally formed with the sleeve 50 is an internally projecting annular rib 60 having radially facing opposite sides except in the area where the ribs 60 intersect the tracks 54 where the sides of the ribs 60 are beveled at 62 as best seen in the hidden lines in FIG. 8.

An adaptor hub 70 having a cylindrical wall 72 and preferably three pairs of spaced external follower projections 74 is provided for assembly at the factory into the sleeve 50 to occupy an assembled position in the sleeve abutting the sleeve collar 56 proximate the aperture 58. The adaptor hub 70 has an internal passageway sized to axially receive the nozzle end 30 of a medical syringe inserted into the adaptor hub. Internal male screw threads 76 are provided in the adaptor 70 each having a sharp leading end 78 for penetrating the relatively soft polypropylene material of the syringe nozzle end 30 during rotation of the adaptor hub relative to the syringe when the nozzle end 30 is screwed into the adaptor hub. The entire adaptor hub 70 is preferably made of a hard material such as medical grade polycarbonate so that the sharpened threads 76 dig into and self thread onto the relatively soft polypropylene material of the nozzle end 30 of the syringe. It will be noted that each of the internal threads 76 also has a terminal end which includes a radially extending abutment surface 76a which prevents reverse rotation of the adaptor hub 70 relative to the syringe after the adaptor hub 70 has been connected to the syringe at the nozzle end 30.

Figure 5:
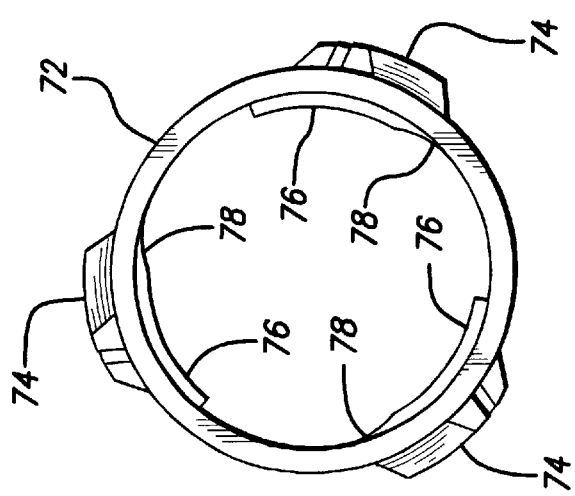
FIG. 5 is an end view of the adaptor hub.
Figure 3:
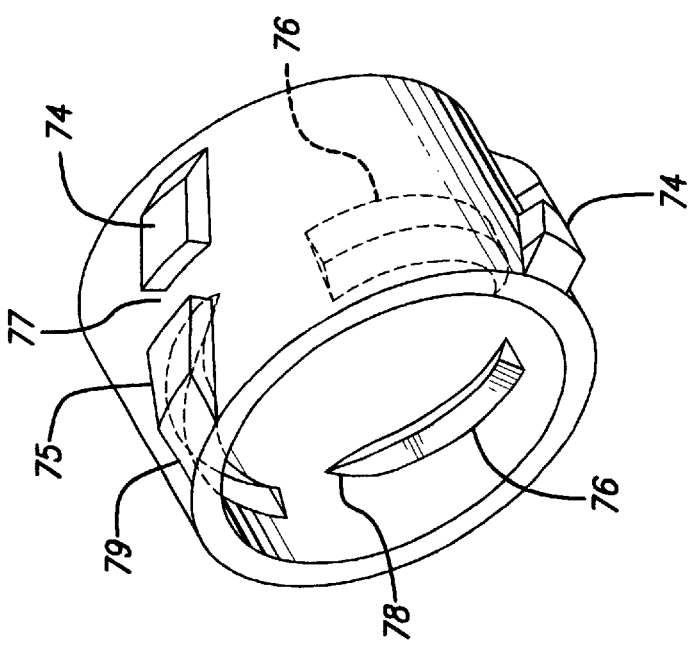
FIG. 3 is a perspective view of the adaptor hub.
Figure 6:
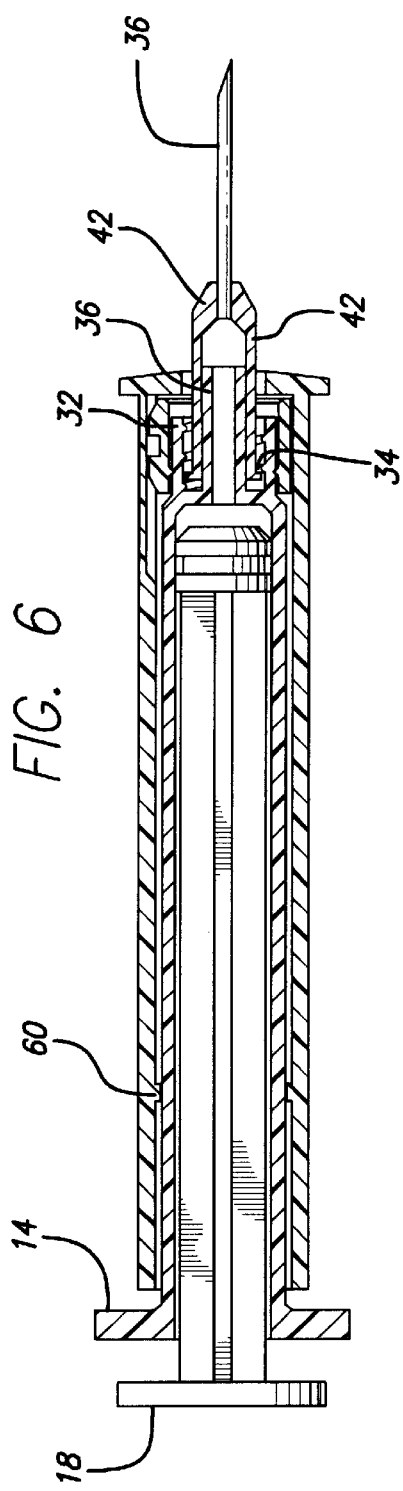
FIG. 6 is a cross sectional view of the syringe with the adaptor hub and protective sheath assembled thereon and with the syringe needle exposed for use.
Figure 7:
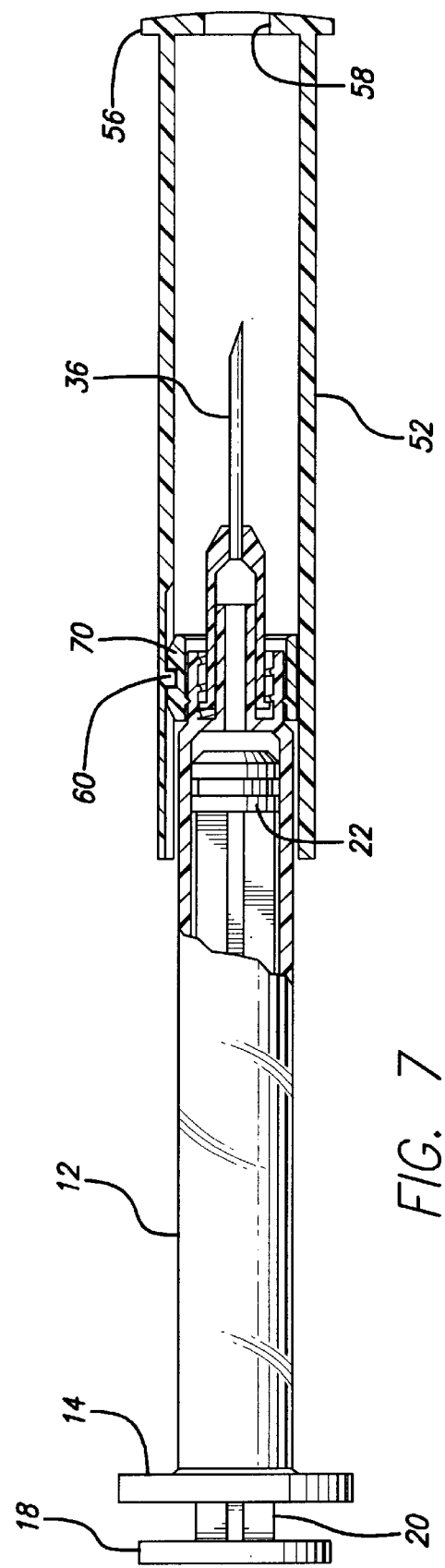
FIG. 7 is a cross sectional view of the syringe with the adaptor hub and protective sheath assembled thereon and with the syringe needle withdrawn after use into the protective sheath for safe disposal.

As best seen in FIGS. 3–5 the spaced external projections 74 on the adaptor hub 70 include three equally circumferentially spaced pairs of follower projections 74. The projections 74 of each pair thereof are spirally aligned on the outer surface of the adaptor 70 at the same spacing and pitch as the tracks 54 so that the followers will follow without binding in the tracks 54. The follower projections 74 of each pair are also axially spaced apart to provide generally annularly extending recesses 77 therebetween of width slightly greater than the width of the annular internal rib 60 in the protective sleeve 50 so that radially extending surfaces on the followers 74 on each side of the recesses will engage with and abut the radially extending surfaces of the rib 60 when the syringe and attached needle 46 is withdrawn after use to retain and completely contain the needle within the protective sleeve 50. During movement of the syringe and attached needle and adaptor hub 70 relative to the protective sleeve 50, the external follower projections 74 on the adaptor hub 70 follow the spaced internal spiral tracks 54 on the interior surface of the sleeve 50 until such time as the annularly extending adaptor recesses 77 engage the rib 60 following which the syringe and protective sleeve are locked together with the used and therefore contaminated needle 46 completely enclosed and retained in the protective sleeve 50. In the preferred embodiment, the rib 60 is provided on the interior cylindrical surface of the sleeve 50 and the recesses 77 are provided on the exterior surface of the hub by spirally spacing the follower projections 74 from each other.

Preferably, the spiral tracks 54 and follower projections 74 are oriented to cause clockwise movement of the sleeve 50 relative to the syringe 10 as the needle 46 is withdrawn into the protective sleeve 50.

The protective sleeve 50 and adaptor hub 70 can be assembled together and marketed as a combination for affixation to conventional non-safety syringes by hospital or other medical personnel to thus retrofit existing unprotected syringes with a protective sleeve and adaptor hub combination to convert them to safety syringes. Alternatively, safety syringes can be assembled at the factory by connecting non-safety syringes 10 to pre-assembled protective sleeves 50 and adaptor hubs 70 seated in the protective sleeves abutting the collars 56. When sold as a separate combination, the protective sleeve and adaptor hub need not comprise a sterile product since the protective sleeve and adaptor hub combination has no interference or contact with the fluid path of the syringe. Although it is preferable to construct the entire adaptor hub 70 of relatively hard material such as polycarbonate, persons skilled in the art will appreciate that the adaptor hub 70 can itself be constructed of softer material so long as the internal male threads 76 therein are of a sharpness and hardness suitable for penetrating the relatively soft material such as polypropylene of a typical syringe during rotation of the adaptor hub relative to the syringe nozzle end 30 as the adaptor hub and attached sleeve 50 are screwed onto the nozzle end 30. Accordingly a simple two-part easily manufacturable device has been provided which is easily attachable to conventional syringes to create a protective enclosure for the syringe needle 46 following use thereof to minimize risk of harm to medical personnel.

While the foregoing constitutes a complete description of the preferred embodiment, it will be appreciated by persons skilled in the art that modifications can be made from the preferred embodiment and the scope of protection is defined by the following claims.

What is claimed is:

1. A protective sleeve and adaptor hub combination for affixation to a medical syringe to enclose a needle affixed to the syringe following use thereof, said combination comprising:

a) an elongate generally cylindrical protective sleeve for telescopically enclosing a syringe, said sleeve having a track on an interior surface for receiving an external follower projection on an adaptor hub as said sleeve is affixed to said adaptor hub; and b) a generally cylindrical adaptor hub for reception in said sleeve, said hub sized to internally receive a conventionally configured nozzle end of a medical syringe axially in said adaptor hub, said adaptor hub having at least one internal male screw thread having a sharp leading end for penetrating relatively soft material of a conventionally configured syringe nozzle end during rotation of said adaptor hub relative to the nozzle end as a nozzle end of a syringe is screwed into said adaptor hub, said thread also having a terminal end which includes an abutment surface to prevent reverse rotation of said adaptor hub relative to the syringe, said adaptor hub further having at least one external follower projection on an exterior surface for engagement with said track in said sleeve for guiding said hub in said sleeve for movement longitudinally of said sleeve; and c) said sleeve and said hub having an engageable mating annular rib and recess for restraining axial movement of said hub and an attached syringe in said sleeve.

2. The sleeve and adaptor hub combination of claim 1, wherein said adaptor hub is made of medical grade polycarbonate and said sleeve is made of polypropylene.

3. The sleeve and adaptor hub combination of claim 1, wherein said adaptor hub includes a plurality of spaced ones of said internal threads each having a sharpened end facing in the same circumferential direction.

4. The sleeve and adaptor hub combination of claim 3, wherein said adaptor hub includes three of said internal threads.

5. The sleeve and adaptor hub combination of claim 1, wherein said track on an interior surface of said sleeve comprises a spiral groove.

6. The sleeve and adaptor hub combination of claim 5, including a plurality of said external projections and grooves, each external projection on said adaptor hub being spirally arranged on an external surface of said hub and sized to be received in and follow a corresponding groove in said sleeve, said external projections and grooves being circumferentially spaced at substantially equal intervals.

7. The sleeve and adaptor hub combination of claim 6, wherein said adaptor hub includes three of said external projections.

8. The sleeve and adaptor hub combination of claim 1, wherein said annular rib is on said interior surface of said protective sleeve and said recess is defined by spaced ones of said projections on said hub.

9. The sleeve and adaptor hub combination of claim 8, wherein said rib and said projections have radially extending side surfaces for abutment with each other to hold said hub in engagement with said rib when a syringe needle is withdrawn into said sleeve, said rib having beveled sides at the intersections of said rib and said tracks and said projections on said hub having beveled surfaces engageable with said beveled sides of said rib for permitting said hub to pass said rib.

10. A medical syringe including a housing having a nozzle end, a plunger in said housing and a needle affixed to said nozzle end, a protective outer sleeve for enclosing said needle following use thereof, said protective sleeve telescopically enclosing said syringe housing, and an adaptor hub affixed to said nozzle end and said outer sleeve, said adaptor hub internally receiving said nozzle end axially in said adaptor hub, said adaptor hub having at least one internal male screw thread having a hard sharp leading end penetrating relatively soft material of said nozzle end during rotation of said adaptor hub relative to said syringe as said nozzle end hub is screwed into said adaptor hub, said thread also having a terminal end which includes an abutment surface to prevent reverse rotation of said adaptor hub relative to said syringe, said sleeve having a track on an interior surface and said adaptor hub having at least one follower projection on an exterior surface engaged with said track in said sleeve for guiding said hub in said sleeve for movement longitudinally of said sleeve, and said sleeve and said hub having an engageable mating rib and recess for restraining axial movement of said hub and attached syringe in said sleeve.

11. The syringe of claim 10, wherein said adaptor hub is made of medical grade polycarbonate and said syringe housing is made of polypropylene.

12. The syringe of claim 10, wherein said adaptor hub includes a plurality of spaced ones of said internal threads each having a sharpened end facing in the same circumferential direction.

13. The syringe of claim 12, wherein said adaptor hub includes three of said internal threads.

14. The syringe of claim 13, wherein said track on an interior surface of said sleeve comprises a spiral groove.

15. The syringe of claim 14, including a plurality of said external projections and grooves, each external projection on said adaptor hub being spirally arranged on an external surface of said hub and sized to be received in and follow a corresponding groove in said sleeve, said external projections and grooves being circumferentially spaced at substantially equal intervals.

16. The syringe of claim 15, wherein said adaptor hub includes three of said external projections.

17. The syringe of claim 10, wherein said annular rib is on said interior surface of said protective sleeve and said recess is defined by spaced projections on said hub.

18. The syringe of claim 17, wherein said rib and said projections have radially extending side surfaces for abutment with each other to hold said hub in engagement with said rib when a syringe needle is withdrawn into said sleeve, said rib having beveled sides at the intersections of said rib and said tracks and said projections on said hub having beveled surfaces engageable with said beveled sides of said rib for permitting said hub to pass said rib.

\* \* \* \* \*